(12) United States Patent
Serres Piole et al.

(10) Patent No.: US 10,080,980 B2
(45) Date of Patent: Sep. 25, 2018

(54) METHOD FOR ISOLATING DIAMONDOIDS

(71) Applicant: TOTAL SA, Courbevoie (FR)

(72) Inventors: Coralie Serres Piole, Pau (FR); Jean-Bernard Berrut, Pau (FR)

(73) Assignee: TOTAL SA, Courbevoie (FR)

( * ) Notice: Subject to any disclaimer, the term of this patent is extended or adjusted under 35 U.S.C. 154(b) by 248 days.

(21) Appl. No.: 14/651,428

(22) PCT Filed: Dec. 10, 2013

(86) PCT No.: PCT/EP2013/076100
§ 371 (c)(1),
(2) Date: Jun. 11, 2015

(87) PCT Pub. No.: WO2014/090809
PCT Pub. Date: Jun. 19, 2014

(65) Prior Publication Data
US 2015/0336860 A1    Nov. 26, 2015

(30) Foreign Application Priority Data

Dec. 11, 2012  (FR) ..................... 12 61891

(51) Int. Cl.
| | |
|---|---|
| *B01J 20/286* | (2006.01) |
| *C07C 7/135* | (2006.01) |
| *C07C 7/12* | (2006.01) |
| *C07C 7/13* | (2006.01) |
| *C07C 7/152* | (2006.01) |
| *B01D 15/38* | (2006.01) |
| *B01D 15/18* | (2006.01) |
| *C07C 7/00* | (2006.01) |

(52) U.S. Cl.
CPC ..... *B01D 15/3828* (2013.01); *B01D 15/1871* (2013.01); *B01J 20/286* (2013.01); *C07C 7/005* (2013.01); *C07C 7/12* (2013.01); *C07C 7/13* (2013.01); *C07C 7/152* (2013.01); *B01J 2220/80* (2013.01); *C07C 2603/74* (2017.05); *C07C 2603/90* (2017.05)

(58) Field of Classification Search
None
See application file for complete search history.

(56) References Cited

U.S. PATENT DOCUMENTS

| | | | |
|---|---|---|---|
| 4,426,292 A | 1/1984 | Wernick et al. | |
| 4,952,749 A | 8/1990 | Alexander et al. | |
| 2002/0177743 A1* | 11/2002 | Dahl | C07C 4/00 585/16 |
| 2005/0159634 A1* | 7/2005 | Dahl | B82Y 10/00 585/17 |
| 2017/0130163 A1* | 5/2017 | Kelliher | B01D 15/185 |

FOREIGN PATENT DOCUMENTS

WO     WO 2014/090809     6/2015

OTHER PUBLICATIONS

International Search Report and Written Opinion dated Apr. 17, 2014 (and its English translation) for PCT Application No. PCT/EP2013/076100 filed Dec. 10, 2013 (published as WO 2014/090809 and Jun. 19, 2014) which is the parent application to the instant application; 17 pages.

Ling Huang et al: "A novel method for isolation of diamondois from crude oils for compound-specific isotope analysis", Organic Geochemistry, Pergamon, Amsterdam, NL, vol. 42, No. 5, Feb. 24, 2011, pp. 566-571.

* cited by examiner

*Primary Examiner* — Tam M Nguyen
(74) *Attorney, Agent, or Firm* — Harness, Dickey & Pierce, P.L.C.; Anthony G. Fussner (57) ABSTRACT

Method for separating the diamondoids by liquid chromatography from a sample of iso-alkanes and cycloalkanes, or from a mixture of organic compounds, this method comprising introducing the sample into a column comprising a stationary phase comprising a material capable of forming inclusion complexes with the diamondoids, eluting with an eluent, and collecting the eluted fraction.

10 Claims, 3 Drawing Sheets

METHOD FOR ISOLATING DIAMONDOIDS

CROSS REFERENCE TO RELATED APPLICATIONS

This patent application is a U.S. national stage filing under 35 U.S.C. § 371 of International Application No. PCT/EP2013/076100 filed Dec. 10, 2013 (published as WO 2014/090809 on Jun. 19, 2014, which claims priority to and benefit of France application No. 1261891 filed Dec. 11, 2012. The disclosures of the applications identified in this paragraph are incorporated herein by reference in their entirety.

FIELD OF THE INVENTION

The present invention relates to a method for separating diamondoids by liquid chromatography from a sample of iso-alkanes and cycloalkanes.

The present invention also relates to a method for isolating diamondoids from a mixture of organic compounds, this method implementing the abovementioned separation method.

The present invention also relates to a kit and a device allowing the isolation of diamondoids by liquid chromatography from a mixture of organic compounds.

The invention also relates to the use of such a kit or such a device for separating diamondoids from a sample of iso-alkanes and cycloalkanes or from a mixture of organic compounds.

TECHNICAL BACKGROUND

Petroleum is a mineral oil formed by a mixture of organic compounds trapped in very diverse geological formations. Thus, each petroleum deposit holds a particular quality of petroleum, determined by the relative proportions of the different organic compounds of which it is constituted.

These organic compounds are essentially hydrocarbons, including saturated compounds: the n-alkanes, iso-alkanes and cycloalkanes, aromatic compounds, resins or also asphaltenes.

Among the cycloalkanes, the diamondoids, tricyclic terpanes, hopanes, steranes may be mentioned. Among the iso-alkanes, pristane and phytane may be mentioned.

The diamondoids are 3-dimensional polycyclic saturated organic compounds. The diamondoids are presented in the form of a cage and can be substituted, or unsubstituted, by alkyl groups. Among these diamondoids, adamantane ($C_{10}H_{16}$ compound), diamantane ($C_{14}H_{20}$) or also triamantane ($C_{18}H_{24}$) may be mentioned non-limitatively, as well as their homologues comprising at least one alkyl branch.

These diamondoids are therefore natural constituents of petroleum, which is also referred to as "oil" in the remainder of the present description. The diamondoids are commonly found in oils at concentrations greater than 1 ppm.

Because of their unique physico-chemical properties (high thermal stability, high melting and vapour pressure points), there has for several years been growing interest in the diamondoids in a large number of fields (pharmaceuticals industry, medicine, nanotechnology, micro-electronics etc.) including the petroleum sector (G. Ali Mansoori, Advances in Chemical Physics, 136, 207-258, 2007). It is therefore very beneficial to isolate, purify and concentrate these diamondoids for subsequent use of the latter, in particular in the fields which have just been mentioned.

Moreover, due to their high stability in oils, it is beneficial to carry out analyses, both qualitative and quantitative, of these diamondoids in order to have a better understanding of petroleum systems, in particular of biodegraded and cracked oils. Such analyses make it possible in particular to evaluate the geological maturity of an oil field and/or the level of thermal maturity of oils, to distinguish between two oils and/or to characterize mixtures of oils, to evaluate the degree of advancement of biodegradation of the oils, to determine the oil/oil or source rock/oil correlations. This explains the increase in the number of studies carried out aimed at isolating and identifying these diamondoids.

Such qualitative and/or quantitative analyses are in general carried out by gas chromatography (GC) or by gas chromatography coupled with mass spectrometry (GC/MS). As for the isotopic analyses, they are carried out by gas chromatography coupled with isotopic ratio mass spectrometry (GC/irMS).

However, in view of the large variety of compounds forming the oil and the very small quantity of these compounds of interest within an oil, it proves necessary to prepare the sample of oil before carrying out its chromatographic analysis (by GC, GC/MS or GC/irMS) in order to purify, isolate and/or concentrate the specific compounds that are to be studied.

The methods described in the literature for isolating the diamondoids, whether from isolated fractions of iso-alkanes and cycloalkanes, or from an oil, are relatively complex.

Reference can in particular be made to the scientific publication by L. Huang et al. ("*A novel method for isolation of diamondoids from crude oils for compound-specific isotope analysis*"—Organic Geochemistry—42 (2011) p. 566-571) which describes a method for separating the diamondoids from a sample of crude oil. This method comprises the following successive steps:

a first separation step by liquid chromatography, through a column comprising an activated silica gel, in order to collect a saturated fraction of hydrocarbons comprising the n-alkanes and the cyclic and branched hydrocarbons, a step of concentration under nitrogen of this saturated fraction of hydrocarbons, a second separation step of this concentrated saturated fraction of hydrocarbons by liquid chromatography, through a column comprising a molecular sieve (Zeolite ZSM-5 of silicalite type), in order to collect the fraction of cyclic and branched hydrocarbons, a third step of separation of the diamondoids from the cyclic and branched hydrocarbon fraction, this third step being based on the inclusion, in β-cyclodextrin, of the diamondoids contained in the cyclic and branched hydrocarbon fraction, then the destruction of the cyclodextrin polymer by acid hydrolysis.

The third step of separation described in the publication by L. Huang et al. involves the implementation of the following successive operations:

mixing, under stirring for at least two hours, the cyclic and branched hydrocarbon fraction collected after the second separation step, with β-cyclodextrin in solution in deionized water, separating, by centrifugation, the precipitate formed during mixing, washing the precipitate with cyclohexane, solubilizing the washed precipitate in a dilute HCl solution, heating (at 80° C. for at least 4 hours) the above solution in order to obtain the β-cyclodextrin acidolysis reaction, after cooling down the solution, extracting the diamondoids using cyclohexane, after washing the extracted solution with deionized water, then drying with $Na_2SO_4$, the solution containing the diamondoids was concentrated under a nitrogen flow.

This concentrated solution is then analyzed by gas chromatography coupled with mass spectrometry (GC/MS). If the publication of L. Huang et al. reports a separation of the diamondoids from the cyclic and branched hydrocarbon fraction, which is carried out successfully, the fact remains that the increase in the number of operations increases the time necessary to obtain the sought compounds, which necessarily has an impact on obtaining the results of the subsequent analyses to be carried out on these products.

This increase in the number of operations furthermore leads to a very low recovery yield. The latter is typically less than 10% of the initial diamondoids content present in the crude oil Finally, the increase in the number of operations inevitably increases the risks of the loss and/or contamination of the samples.

Cyclodextrins, which are obtained by the enzymatic degradation of starch, are cyclic oligosaccharides which can comprise from six to eight glucose units. A distinction is thus made between three families of cyclodextrins depending on the number of glucose units forming the oligosaccharide: these families are denoted α, β and γ when they comprise six, seven and eight glucose units respectively.

The cyclodextrins, and more particularly the β-cyclodextrins, are known to form inclusion complexes in aqueous solutions with a large variety of polar and non-polar compounds, including the aromatic hydrocarbons and compounds comprising a heteroatom. The internal cavity of β-cyclodextrin, which is essentially formed by carbon atoms and hydrogen, is fairly hydrophobic whereas the external surfaces are hydrophilic in so far as all the hydroxyl groups of the glucose units are turned towards the outside of the molecule. The internal diameter of the hydrophobic cavity of β-cyclodextrin is comprised between 6.0 and 8.5 Å.

As reported in the publications by G. Ali Mansoori ("*Diamondoid molecules*"—Advances in Chemical Physics—136 (2007) p. 207-258) and by C. Leggio et al. ("*Study on the structure of host-guest supramolecular polymers*"—Macromolecules–40 (2007) p. 5899-5906), adamantane, because of its size, is inserted with very good adjustment into the cavity of cyclodextrin and, more particularly, of β-cyclodextrin.

The purpose of the present invention is to provide a method for isolating by liquid chromatography compounds belonging to the family of the diamondoids, whether from a sample of cycloalkanes optionally containing iso-alkanes, or more generally from a sample of a mixture of organic compounds, this method at least partially overcoming the abovementioned drawbacks.

More particularly, the invention relates to a method which makes it possible to isolate diamondoids from such a sample of cycloalkanes optionally containing iso-alkanes, or more generally from a mixture of organic compounds, with a minimum number of operations, without the risk of contamination of the samples and/or the loss of the compounds, and in a reasonable time compatible with carrying out qualitative, quantitative and/or subsequent isotopic analyses.

SUMMARY OF THE INVENTION

For this purpose, a subject of the present invention is a method for isolating diamondoids from a sample of iso-alkanes and cycloalkanes comprising a separation step by liquid chromatography, this separation step comprising:

introducing the sample into a column comprising a stationary phase comprising a material capable of forming inclusion complexes with diamondoids, eluting with an eluent, and collecting the eluted fraction.

Throughout the following description of the method of the invention, when it is stated that the method starts from a sample of cycloalkanes, it is provided that the latter can also comprise iso-alkanes. According to a preferred variant, the method is implemented starting from a mixture of cycloalkanes and iso-alkanes.

According to preferred embodiments, the invention comprises one or more of the following features:

the material capable of forming inclusion complexes with diamondoids is selected from the cyclodextrins.

the material capable of forming inclusion complexes with diamondoids is β-cyclodextrin.

the eluent is selected from mixtures of n-alkane and alkanol, advantageously selected from mixtures of C3-C8 n-alkane and C1-C4 alkanol with an alkane/alkanol volume ratio ranging from 90/10 to 99.5/0.5.

the eluent is a pentane/isopropanol mixture (98%/2% vol/vol).

the column is an HPLC column connected to an HPLC device, the method being implemented with a pressure in the column ranging from 10 to 30 bars, advantageously from 15 to 25 bars.

The present invention makes it possible to overcome the drawbacks of the methods of the prior art. It provides more particularly a method for separating a fraction of diamondoids from a sample of cycloalkanes, which is both simple and rapid, comprising a number of steps limited with respect to the third separation step of the method described in the scientific publication by L. Huang et al. cited above. The separation method according to the invention makes it possible in particular to avoid the risks of contamination and the loss of certain diamondoid compounds present in the sample of cycloalkanes, risks which are inherent in the increase in the number of operations of this method of the prior art.

This result is achieved by means of the implementation of a separation step by liquid chromatography carried out by means of a column comprising a stationary phase of a material capable of forming an inclusion complex with diamondoids, in particular this material can be a cyclodextrin.

The selection of a separation by liquid chromatography with a stationary phase comprising a material capable of forming an inclusion complex with diamondoids makes it possible to isolate the diamondoids in a very reduced number of operations compared with the methods of the prior art. By means of the method according to the invention, the recovery of the diamondoids from a sample of cycloalkanes is carried out in a much shorter time than with the method of the prior art and under more reliable conditions of implementation, i.e. with a clearly reduced risk of contamination and/or losses compared with that inherent in the method of the prior art. Finally, the speed and the high yields of the method of the invention make it possible to envisage its application for preparative purposes.

The present invention also relates to a method for separating a fraction of diamondoids from a sample of a mixture of organic compounds, this method comprising the following steps:

a first step of separation by liquid chromatography of a fraction of iso-alkanes and cycloalkanes from the mixture of organic compounds, optionally a preparation step of the fraction of iso-alkanes and cycloalkanes, and a second step of separation of diamondoids from a sample of iso-alkanes and cycloalkanes according to the method as described above.

According to preferred embodiments, the invention comprises one or more of the following features:

The method comprises:

introducing the mixture of organic compounds into a column comprising at least two stationary phases, the first stationary phase being of a material capable of adsorbing the acyclic apolar compounds and the second stationary phase being of a material capable of adsorbing the aromatic compounds and the polar compounds, eluting with an eluent, and collecting the fraction or fractions of eluted iso-alkanes and cycloalkanes.

the first stationary phase is of a material capable of adsorbing the n-alkanes and, advantageously, comprises a zeolite, the second stationary phase is of a material capable of adsorbing the aromatic and polar compounds and, advantageously, comprises a silica impregnated with silver nitrate.

the column also comprises a third stationary phase of a material capable of adsorbing the compounds in which the polarity is greater than the polarity of the compounds adsorbed by the material of the second stationary phase, and, advantageously, comprises a silica selected from a virgin silica, a silica grafted with aminoalkyl groups, in particular aminopropyl groups and a silica grafted with cyanoalkyl groups and preferentially with cyanopropyl groups.

the first separation step is a step of separation by low pressure chromatography, in which the liquid phase is eluted under a pressure of less than 25 bars, advantageously comprised between 3 and 10 bars and, preferably, comprised between 7 and 9 bars.

the eluent is selected from iso-octane, n-octane and mixtures thereof, advantageously iso-octane.

the method comprises an intermediate step of preparation of the fraction of iso-alkanes and cycloalkanes, this preparation comprising filtration and/or concentration by partial evaporation of the solvent.

The separation methods according to the invention, which make it possible to isolate the diamondoids from a sample of cycloalkanes or, more generally, from a mixture of organic compounds, also have the advantage of being easily reproducible and providing reliable results within clearly shorter periods of time than those of the methods of the prior art.

The invention also relates to a kit and a device allowing the isolation of diamondoids by liquid chromatography. Such a kit comprises:

a first column (1) comprising at least two stationary phases, the first stationary phase (11) being of a material capable of adsorbing the acyclic apolar compounds and the second stationary phase (12) being of a material capable of adsorbing the aromatic compounds and the polar compounds, optionally a third stationary phase (13) of a material capable of adsorbing the compounds in which the polarity is greater than the polarity of the compounds adsorbed by the material of the second stationary phase, and a second column (2) comprising a stationary phase (16) of a material capable of forming inclusion complexes with diamondoids.

According to preferred embodiments, the kit according to the invention comprises one or more of the following features:

the material capable of forming inclusion complexes with diamondoids is β-cyclodextrin.

the kit comprises one or more means selected from:

means (20) making it possible to connect the first column (1) to pressurizing means (22), means (34) making it possible to connect the second column (2) to an HPLC device (29), means (23, 34) allowing the introduction of the samples into each of the columns (1, 2), means (26, 33) for collecting samples, means (25, 32) of analysis.

The invention also relates to a device allowing the isolation of diamondoids from a sample of a mixture of organic compounds. Such a device comprises:

a first column (1) comprising at least two stationary phases, the first stationary phase (11) being of a material capable of adsorbing the acyclic apolar compounds and the second stationary phase (12) being of a material capable of adsorbing the aromatic compounds and the polar compounds, optionally a third stationary phase (13) of a material capable of adsorbing the compounds in which the polarity is greater than the polarity of the compounds adsorbed by the material of the second stationary phase, and a second column (2) comprising a stationary phase (16) of a material capable of forming inclusion complexes with diamondoids, means (14, 23) for introducing the sample into the first column (1), means (22) for introducing a first eluent into the first column (1), optionally means (21) for pressurizing the first column (1), optionally means (25) for detecting and analyzing the eluted fractions leaving the first column (1), means (26) for collecting the eluted fractions leaving the first column (1), means (34) for introducing the eluted fractions leaving the first column (1) into the second column, means (28, 30) for introducing a second eluent into the second column (2), means (29) for pressurizing the second column (2), optionally means (32) for detecting and analyzing the eluted fractions leaving the second column (2), and means for collecting the eluted fractions leaving the second column.

optionally means (35, 36) for monitoring and automation of the method, in particular means allowing the monitoring of the introduction of the samples into the columns, and/or the recovery of the eluted fractions leaving the column, and/or the monitoring of the analysis means, and/or the retrieval and storage of the analytical data, According to a particular embodiment, the method for the separation of the diamondoids from a mixture of organic compounds according to the invention is implemented by means of the kit and/or by means of the device according to the invention, in particular when the mixture of organic compounds is a crude petroleum or an oil or an oily mixture originating from the treatment of the petroleum, in particular by refining.

The invention also relates to a use of the kit and/or of the device for separating the diamondoids from a mixture of organic compounds, this mixture can in particular originate from a deposit of crude oil, shale oils or petroleum cuts.

BRIEF DESCRIPTION OF THE FIGURES

FIG. 3 is a chromatogram representing the ELSD (Evaporative Light

Scattering Detection) analysis of 8 pure standards in solution in iso-octane and the differential refractometry (DR) analysis of adamantane in solution in iso-octane.

In order to allow the identification of the diamondoids identified by their commonly used abbreviation as it appears in FIG. 4, reference can be made to Table 1 below which specifies, for each diamondoid, its empirical formula, its CAS registry number as well as its abbreviation.

TABLE 1

| Compounds | Abbreviations | Empirical formula | CAS No. |
|---|---|---|---|
| Adamantane | A | $C_{10}H_{16}$ | 281-23-2 |
| 1-Me-adamantane | 1-MA | $C_{11}H_{18}$ | 768-91-2 |
| 1,3-diMe-adamantane | 1,3-dMA | $C_{12}H_{20}$ | 702-79-4 |
| 1,3,5-triMe-adamantane | 1,3,5-tMA | $C_{13}H_{22}$ | 707-35-7 |
| 1,3,5,7-tetraMe-adamantane | 1,3,5,7-tetraMA | $C_{14}H_{24}$ | 1687-36-1 |
| 2-Me-adamantane | 2-MA | $C_{11}H_{18}$ | 700-56-1 |
| Cis-1,4-diMe-adamantane | 1,4-dMA,cis | $C_{12}H_{20}$ | 24145-89-9 |
| Trans-1,4-diMe-adamantane | 1,4-dMA,trans | $C_{12}H_{20}$ | 24145-88-8 |
| 1,3,6-triMe-adamantane | 1,3,6-tMA | $C_{13}H_{22}$ | 24139-37-5 |
| 1,2-diMe-adamantane | 1.2dMA | $C_{12}H_{20}$ | 16207-81-1 |
| Cis-1,3,4-triMe-adamantane | 1,3,4-tMA,cis | $C_{13}H_{22}$ | 24145-90-2 |
| Trans-1,3,4-triMe-adamantane | 1,3,4-tMA,trans | $C_{13}H_{22}$ | 24145-91-3 |
| 1.2,5,7-tetraMe-adamantane | 1.2,5,7-tetraMA | $C_{14}H_{24}$ | 34946-70-7 |
| 1-Et-adamantane | 1-EA | $C_{12}H_{20}$ | 770-69-4 |
| 1-Et-3-Me-adamantane | 1-E-3-MA | $C_{13}H_{22}$ | 1687-34-9 |
| 1-Et-3,5-diMe-adamantane | 1-E-3,5-dMA | $C_{14}H_{24}$ | 1687-35-0 |
| 2-Et-adamantane | 2-EA | $C_{12}H_{20}$ | 14451-87-7 |
| Diamantane | D | $C_{14}H_{20}$ | 2292-79-7 |
| 4-Me-diamantane | 4-MD | $C_{15}H_{22}$ | 28375-86-2 |
| 4,9-diMe-diamantane | 4,9-dMD | $C_{16}H_{24}$ | 70459-27-7 |
| 1-Me-diamantane | 1-MD | $C_{15}H_{22}$ | 26460-76-4 |
| 1,4 and 2,4-diMe-diamantane | 1,4 & 2,4-dMD | $C_{16}H_{24}$ | 74340-66-8 74340-67-9 |
| 4,8-diMe-diamantane | 4,8-dMD | $C_{16}H_{24}$ | 70340-68-0 |
| TriMe-diamantane | tMD | $C_{17}H_{26}$ | |
| 3-Me-diamantane | 3-MD | $C_{15}H_{22}$ | 30545-28-9 |
| 3,4-diMe-diamantane | 3,4-dMD | $C_{16}H_{24}$ | 70340-69-1 |
| Triamantane | T | $C_{18}H_{24}$ | 13349-10-5 |
| 9-Me-triamantane | 9-MT | $C_{19}H_{26}$ | 67615-85-4 |
| DiMe-triamantane | dMT | $C_{21}H_{30}$ | |

DETAILED DESCRIPTION

Firstly, the invention relates to a method for separating the diamondoids from a sample of cycloalkanes optionally containing iso-alkanes, this method comprising a separation step by liquid chromatography, this separation step comprising:
  introducing the sample into a column comprising a stationary phase comprising a material capable of forming inclusion complexes with diamondoids,
  eluting with a solvent or a mixture of solvents, and
  collecting the eluted fractions.

The diamondoids constitute a family of compounds well known to a person skilled in the art. These are polycyclic saturated organic compounds of three-dimensional structure, in the form of a cage, optionally substituted with alkyl groups. Table 1 above shows the main known diamondoids.

The sample of cycloalkanes used as starting material for the method is advantageously obtained from a mixture of organic compounds, in particular of crude petroleum or of an oil or of an oily mixture originating from the treatment of petroleum by a known method, in particular by refining. The mixture of organic compounds originates, directly or after treatment, from a deposit of crude oil, a deposit of shale oil, or of a petroleum cut.

The samples of cycloalkanes used as starting material generally also comprise iso-alkanes. These mixtures of iso-alkanes and cycloalkanes are in fact preferentially obtained by means of a method which allows their separation from a mixture of organic compounds, such as the mixtures of the petroleum derivatives described above. Apart from the diamondoids, the samples of cycloalkanes used as starting material generally comprise the following compounds: among the cycloalkanes, the tricyclic terpanes, hopanes and steranes, and among the iso-alkanes, pristane and phytane may be mentioned.

The chromatography column is selected with suited dimensions to the size of the sample to be treated.

The material capable of forming inclusion complexes with the diamondoids can be selected from those well known to a person skilled in the art for having this property, in particular, the cyclodextrins. The inclusion complexes result from a set of interactions including: the geometric compatibility, the Van der Waals forces, the electrostatic and hydrophobic interactions, and the hydrogen bonds. Among the families of compounds capable of forming inclusion complexes with the diamondoids, thiourea and selenourea may be mentioned (R. Gopal and B. Robertson, Acta, Cryst. (1989), C45, 257-259). Preferably, the material capable of forming inclusion complexes with the diamondoids is selected from α-cyclodextrin, β-cyclodextrin, γ-cyclodextrin. Advantageously this material is β-cyclodextrin.

A preparation step of the mixture of iso-alkanes and cycloalkanes can be provided prior to the separation step. This preparation step can in particular consist of a step of filtration of the sample of iso-alkanes and cycloalkanes and/or a step of concentration by evaporation.

The eluent is selected from the solvents and mixtures of apolar solvents. Preferably it is selected from mixtures of n-alkane and alkanol. Advantageously it is selected from mixtures of C3-C8 n-alkane and C1-C4 alkanol with an alkane/alkanol volume ratio ranging from 90/10 to 99.5/0.5. Generally a mixture of pentane/isopropanol is selected, advantageously with a volume ratio of approximately 98/2.

Advantageously the invention is implemented using an HPLC column connected to an HPLC device (High Performance Liquid Chromatography), which makes it possible to impose a controlled pressure in the chromatography column. Advantageously, the method is implemented with a pressure in the column ranging from 10 to 30 bars, advantageously from 15 to 25 bars, preferably from 17 to 22 bars.

The eluted fractions are recovered on leaving the column. They can then be analyzed. According to another variant, a detector is placed at the outlet of the chromatography column so as to analyze the eluted fractions before their collection. This last variant is preferred as it makes it possible to directly identify the eluted fractions containing the diamondoid compounds. Among the detection means that can be used, evaporative light scattering detection or ELSD, differential refractometry denoted RD, mass spectrometry denoted MS, and specific isotopic analysis of compounds may be mentioned.

By means of the method of the invention, the diamondoids are selectively isolated from a mixture of iso-alkanes and cycloalkanes, the latter being eluted before the diamondoids, because of their lesser affinity with cyclodextrin.

According to a preferred variant, the invention relates to a method for isolating the diamondoids from a mixture of organic compounds by a method comprising the following steps:

a first step of separation by liquid chromatography of a fraction of iso-alkanes and cycloalkanes from the mixture of organic compounds, optionally a preparation step of the fraction of iso-alkanes and cycloalkanes, and a second step of separation of the diamondoids from a sample of iso-alkanes and cycloalkanes according to the method described above.

According to this variant the first step of separation of iso-alkanes and cycloalkanes from the mixture of organic compounds comprises:

introducing the sample into a column comprising at least two stationary phases, the first stationary phase being of a material capable of adsorbing the acyclic apolar compounds and the second stationary phase being of a material capable of adsorbing the aromatic compounds and the polar compounds, eluting with an eluent, and collecting the eluted fraction.

A preparation step of the mixture of organic compounds can be provided prior to the separation step. This preparation step can in particular consist of a step of solubilizing the sample of the mixture with or without a subsequent filtration step. The sample can also be heated. These preparatory steps can also be combined with each other.

The first stationary phase is of a material capable of adsorbing the acyclic apolar compounds, in particular the n-alkanes. The second stationary phase is of a material capable of adsorbing the aromatic compounds and the polar compounds (resins, asphaltenes).

The chromatography column can also comprise a third stationary phase, which is optional, of a material capable of adsorbing the compounds in which the polarity is greater than the polarity of the compounds adsorbed by the material of the second stationary phase, in particular the compounds with a high molecular mass and/or the heteroatomic compounds, in particular the heteroalkyls comprising at least one atom selected from: N, S and O, and/or the resins and asphaltenes with molecular masses comprised between approximately 300 and 10,000 g/mol. A person skilled in the art knows the materials capable of satisfying each of these three conditions and can, by a simple routine test, check if a material is suitable or not for this use. He can in particular test, for each family of compounds, whether or not it is retained on a support, by carrying out an elution test on the test support using a solvent such as iso-octane or octane or a mixture of these solvents. Advantageously, each of the stationary phases is selected so as to retain at least 95% by mass, with respect to the total mass of the sample, of the compounds listed above for each stationary phase respectively, better at least 98%, even better at least 99%.

Advantageously also, the stationary phases are selected so as to allow the elution through the chromatography column of at least 70% by mass, with respect to the total mass of the sample, of the iso-alkane and cycloalkane compounds, and in particular the compounds of interest listed above (in particular diamondoids), better at least 75%, even better at least 80%, preferentially at least 85%, advantageously at least 90%, and even more advantageously at least 95%.

Advantageously, the first stationary phase is of a material capable of adsorbing the n-alkanes, preferably it comprises a zeolite of the sodium aluminosilicate type, advantageously a ZSM-5 zeolite silicalite. Advantageously, the first stationary phase is essentially constituted by a zeolite of the sodium aluminosilicate type, advantageously a ZSM-5 zeolite silicalite.

Preferentially, the second stationary phase is of a material capable of adsorbing the aromatic and polar compounds, and preferably it comprises a silica impregnated with silver nitrate. Preferentially, the second stationary phase is essentially constituted by a silica impregnated with silver nitrate.

Advantageously, the third stationary phase is of a material capable of adsorbing the high molecular weight and/or heteroatomic compounds, in particular the heteroalkyls comprising at least one atom selected from: N, S and O and/or the resins and asphaltenes with molecular masses comprised between approximately 300 and 10,000 g/mol. Preferentially, the third stationary phase comprises a silica selected from a virgin silica, a silica grafted with aminoalkyl groups, in particular aminopropyl groups and a silica grafted with cyanoalkyl groups and preferentially with cyanopropyl groups. Preferentially, the third stationary phase is essentially constituted by a silica selected from a virgin silica, a silica grafted with aminoalkyl groups, in particular aminopropyl groups and a silica grafted with cyanoalkyl groups and preferentially with cyanopropyl groups.

The method for separating iso-alkanes and cycloalkanes from the mixture of organic compounds relates more particularly to the mixtures of organic compounds originating from a deposit of crude oil, shale oils or petroleum cuts. This method relates more particularly to the mixtures of organic compounds comprising, besides one or more compounds as described above and that it is sought to remove, one or more compounds of interest selected in particular from: the cycloalkanes, and the diamondoids, in particular the adamantanes, the diamantanes and the triamantanes, the tricyclic terpanes, hopanes, steranes may be mentioned; iso-alkanes, and pristane and phytane may be mentioned.

The stationary phases are denoted by the name first, second and third stationary phase throughout the description with reference to their order of introduction into the chromatography column. When the chromatography column is eluted, the eluent first passes through the third stationary phase (if present), then the second, then the first stationary phase.

According to a particularly preferred version of the invention, column 1 comprises the following three successive stationary phases 11, 12, 13, listed from the bottom to the top of the column 1, in the opposite direction to the elution direction:

the Zeolite ZSM-5 as first stationary phase 11, this zeolite advantageously being activated by a prior heat treatment, a silica impregnated with silver nitrate as second stationary phase 12, and a silica grafted with cyanopropyl groups as third stationary phase 13.

$M_{P1}$, $M_{P2}$, $M_{P3}$ are denote respectively the masses of the first, the second and the third stationary phases. These masses advantageously satisfy the following relationships.

Preferably $M_{P2} \leq M_{P1} \leq 3\ M_{P2}$
$M_{P3} \leq M_{P1} \leq 5\ M_{P3}$
$M_{P3} \leq M_{P2} \leq 3\ M_{P3}$ Even more preferentially, $M_{P2} \leq M_{P1} \leq 2\ M_{P2}$
$M_{P3} \leq M_{P1} \leq 4\ M_{P3}$
$M_{P3} \leq M_{P2} \leq 2.5\ M_{P3}$ In the example implemented below, the quantities of each stationary phase are the following:

$MP_1 = 3.9$-$4.0$ g
$MP_2 = 2.3$-$2.4$ g
$MP_3 = 1.3$-$1.4$ g

Preferably, the first separation step is a separation step by low pressure chromatography, in which the column is subjected to a pressure of less than 25 bars, advantageously comprised between 3 and 10 bars and, preferably comprised between 7 and 9 bars.

Preferably, in the first separation step the eluent is selected from iso-octane, n-octane and mixtures thereof, advantageously iso-octane.

The collection of the eluted fraction of iso-alkanes and cycloalkanes can be followed directly by its introduction into the chromatography column for the implementation of the second chromatographic separation step.

According to a variant, an intermediate step of preparation of the fraction of iso-alkanes and cycloalkanes can be provided. This intermediate preparation can for example comprise: filtration and/or concentration by partial evaporation of the solvent, dilution.

According to the invention, the method can comprise other steps, such as in particular rinsing one or both columns by means of one or more solvents, in particular before or after the implementation of the method.

The invention also relates to a kit allowing the isolation of the diamondoids by liquid chromatography comprising:

a first column comprising at least two stationary phases, the first stationary phase being of a material capable of adsorbing the acyclic apolar compounds and the second stationary phase being of a material capable of adsorbing the aromatic compounds and the polar compounds, and a second column comprising a stationary phase of a material capable of forming inclusion complexes with diamondoids.

Preferably the first column also comprises a third stationary phase of a material capable of adsorbing the compounds in which the polarity is greater than the polarity of the compounds adsorbed by the material of the second stationary phase.

The favourite materials for producing the kit as well as the arrangement and preferred proportions thereof are those mentioned above for the method.

The kit advantageously comprises means making it possible to connect the first column to pressurizing means, and the second column to the HPLC device envisaged above. It advantageously comprises means allowing the introduction of the samples concerned into each of the columns. It can also comprise means for collecting samples, the detection and analysis means.

A subject of the invention is also a device allowing the isolation of the diamondoids by liquid chromatography comprising:

a first column comprising at least two stationary phases, the first stationary phase being of a material capable of adsorbing the acyclic apolar compounds and the second stationary phase being of a material capable of adsorbing the aromatic compounds and the polar compounds, and a second column comprising a stationary phase of a material capable of forming inclusion complexes with the diamondoids, means for introducing the sample into the first column, means for introducing a first eluent into the first column, optionally means for pressurizing the first column, optionally means for detecting and analyzing the eluted fractions leaving the first column, means for collecting the eluted fractions leaving the first column, means for introducing the eluted fractions leaving the first column into the second column, means for introducing a second eluent into the second column, means for pressurizing the second column, optionally means for detecting and analyzing the eluted fractions leaving the second column, and means for collecting the eluted fractions leaving the second column.

It can also comprise reservoirs for the solvents, for the products to be treated and for the products collected.

The device is advantageously designed in order to allow a continuity between the two separation steps, firstly of a fraction of iso-alkanes and cycloalkanes from an organic mixture, then of the diamondoids from the fraction of iso-alkanes and of cycloalkanes.

In particular, it advantageously comprises means for automating the method, in particular means allowing the monitoring of the introduction of the samples into the columns, and/or the recovery of the eluted fractions leaving the column, and/or the monitoring of the analysis means, and/or the retrieval and storage of the analytical data. Such means (computers and software) are well known to a person skilled in the art.

Among the means for detecting and analyzing the eluted fractions leaving the first column, for example a differential refractometer, a UV detector, a flame ionization detector (FID) or also a mass spectrometer may be mentioned. If the selected analysis means are destructive by nature, a diversion is advantageously provided, by means of a by-pass, upstream of the collection means, in order to channel a small portion of the eluted fractions collected at the base of the column for analysis, the other portion of the eluted fractions being collected in the collection means.

Among the means for detecting and analyzing the eluted fractions leaving the second column, an evaporative light scattering detector or ELSD, a differential refractometer or DR, a mass spectrometer or MS, a UV spectrometer, an irMS spectrometer may be mentioned.

These separation methods according to the invention can be implemented on an analytical scale (a few tens of µl of sample) or on a preparative scale (a few hundred µl of sample). The conditions of separation on an analytical scale by liquid chromatography can be directly extrapolated by a person skilled in the art to a preparative scale by means of routine calculations.

The invention also relates to a method for the separation of the diamondoids from a mixture of organic compounds which is implemented by means of the kit as described above or by means of the device as described above.

DESCRIPTION OF PREFERRED
EMBODIMENTS OF THE INVENTION

Other features and advantages of the invention will become apparent on reading the following description of a preferred embodiment of the invention, given by way of example and with reference to the attached figures.

Separation Kit

Figure 1:
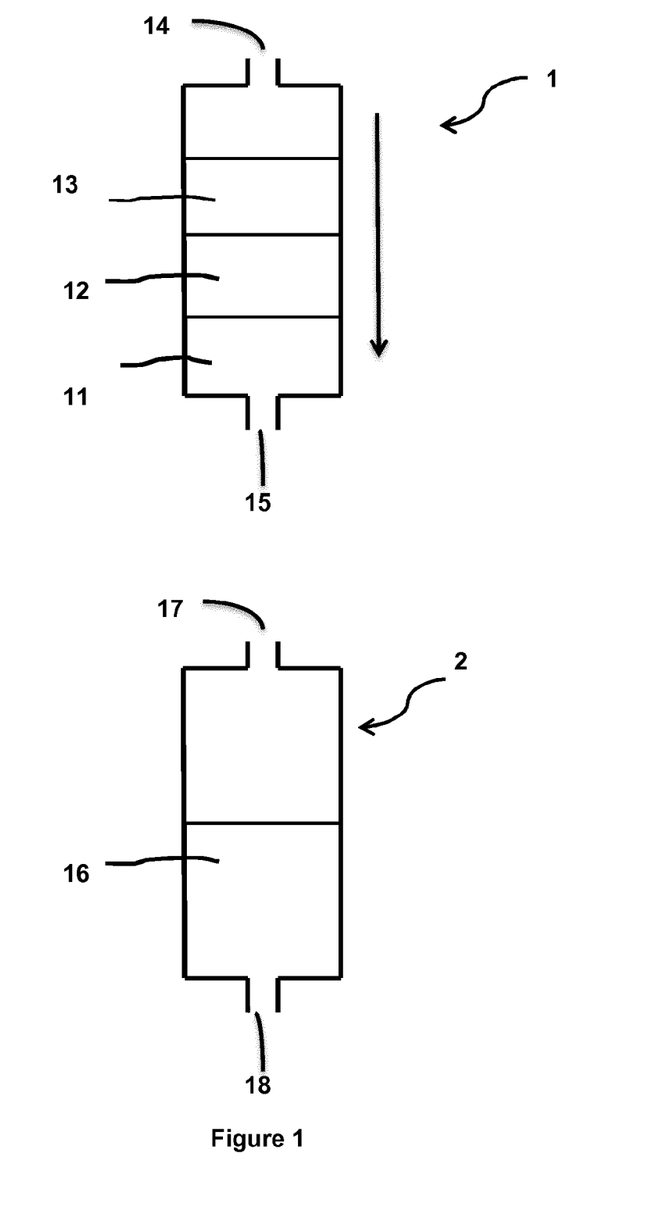
FIG. 1 is a diagrammatic representation of an embodiment of the kit according to the invention.

FIG. 1 represents a schematic diagram of an embodiment of the liquid chromatography separation kit according to the invention.

The kit illustrated in FIG. 1 comprises a first column 1 and a second column 2.

The first column 1 of the kit is a solid phase extraction (SPE) column. It comprises at least two stationary phases.

In the embodiment shown in FIG. 1, which corresponds to an advantageous version of the kit according to the invention, the first column 1 comprises three stationary phases 11, 12 and 13.

The first stationary phase 11 is of a material capable of adsorbing the acyclic apolar compounds of the sample and, more particularly, the n-alkanes. Advantageously, the first stationary phase 11 comprises a zeolite selected from zeolites of the sodium aluminosilicate type, in particular those belonging to the family of the pentasils. Preferably, in these zeolites, the Si to Al molar ratio satisfies: Si/Al/>10. For example the zeolite of ZSM-5 type of chemical formula:

$Na_nAl_nSi_{96-n}O_{192}.16H_2O$ (0<n<27) may be mentioned. These zeolites can be used directly or be activated by a heat treatment.

Preferentially, the first stationary phase comprises a Zeolite ZSM-5 marketed by the company Fisher Scientific. Advantageously, before its implementation, the Zeolite ZSM-5 is activated by heating, in particular heating at a temperature of the order of 360° C. for 12 hours is recommended.

The second stationary phase 12 is of a material capable of adsorbing the aromatic compounds and the polar compounds of the sample (resins, asphaltenes). Advantageously, the second stationary phase 12 comprises a silica impregnated with silver nitrate $AgNO_3$. The silica registered under the CAS number 7761-88-8 can in particular be utilized, having a particle size of 62 μm and a density of 4.35 g/ml at 25° C., this silica being in particular available from the company Sigma Aldrich. This silica impregnated with silver nitrate can be used directly, without prior treatment.

The third stationary phase 13 is of a material capable of adsorbing the compounds of the sample which have a polarity greater than the polarity of the compounds adsorbed by the material of the second stationary phase 12 and, more particularly, the high-molecular-mass and/or heteroatomic compounds, in particular the heteroalkyls comprising one or more atoms selected from: N, S and O. Advantageously, the third stationary phase 13 comprises a silica which can be selected from a virgin silica, a silica grafted with aminoalkyl groups, in particular C1-C5 aminoalkyls, preferably aminopropyls and a silica grafted with cyanoalkyl groups, in particular C1-C5 cyanoalkyls, and, preferentially, with cyanopropyl groups. In particular s silica grafted with cyanopropyl groups can be used, having a particle size comprised between 40 and 63 μm marketed by the companies Merck and VWR. This virgin or grafted silica which are suitable for the third stationary phase 13 can be used directly, without prior treatment.

As shown in FIG. 1, the third stationary phase 13 is arranged above the second stationary phase 12, this second stationary phase 12 being itself arranged above the first stationary phase 11. The arrow represents the direction of elution of the solvent.

The second column 2 of the kit comprises a stationary phase of a β-cyclodextrin material capable of selective inclusion of the diamondoids. The second column comprises an opening 17 allowing the introduction of the sample and an opening 18 making it possible to recover the eluted fraction.

Separation Device

Figure 2:
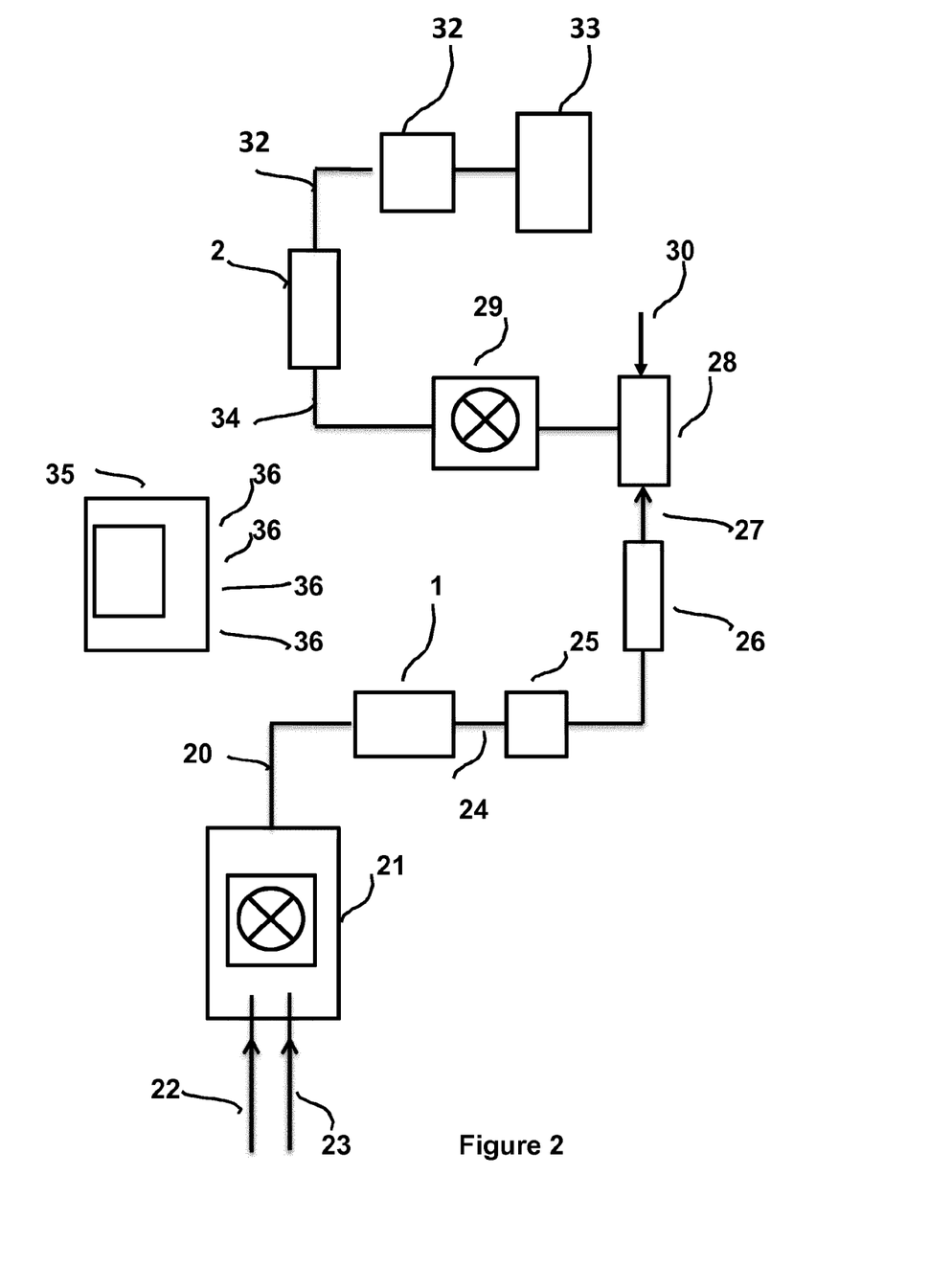
FIG. 2 is a diagrammatic representation of an embodiment of the separation device according to the invention, this device comprising in particular the parts of the separation kit according to the invention.

FIG. 2 represents a schematic diagram of an embodiment of the liquid chromatography separation and analysis device according to the invention, this device comprising the separation kit by chromatography according to the invention as shown in FIG. 1.

The separation device comprises the first column 1 which is connected upstream, by means of connection 20 to a pump system 21. This pump system 21 is itself connected upstream to means 22 for introducing a first eluent (or mobile phase).

The means 23 for introducing the sample of the mixture of organic compounds can be connected at the inlet 14 of the column 1 by means of an injection device situated downstream of the pump system 21 (components not shown in FIG. 1). But, advantageously, and as diagrammatically represented in FIG. 2, the means 23 for introducing the sample are also directly connected to the pump system 21, which has the advantage of limiting the risks of pollution and/or the loss of compounds present in the sample due to the absence of a joint.

The first column 1 is connected, at its outlet 15, by the connection means 24, to the means 25 for the detection and analysis of the compounds forming the eluted fractions. These detection and analysis means 25, which can be constituted by a differential refractometer, are themselves connected to the means 26 for collecting the eluted fractions isolated from the sample.

According to a variant, it can be provided that the separation device according to the invention comprises collection means 26, but not analysis means and that the analysis of the eluted fractions is carried out separately.

The collection means 26 are connected, by introduction means 27, to a degasser 28. itself connected to pressurizing means, such as a high pressure pump 29. The pump 29 is connected to the second column 2.

The column 2 is preferentially a high performance liquid chromatography (HPLC) column.

As shown in FIG. 2, the means for introduction 30 of the second eluent are connected to the degasser 28. However there is nothing to prevent this connection being directly established at the high pressure pump 29.

The second column 2 is connected, at its outlet, by means of connections 31, to means for the detection and analysis 32 of the compounds forming the eluted fractions. These detection and analysis means 32 are themselves connected to means 33 for collecting the eluted fractions isolated from the sample.

These detection and analysis means 32 can be constituted by a differential refractometer (DR) or by an evaporative light scattering detector (ELSD).

Separation Method

The separation method according to the invention can be implemented using the separation device and the kit described above, in particular when it is sought to isolate the diamondoids from a sample of a mixture of organic compounds, such as a sample of crude oil (or petroleum).

First Separation Step by Liquid Chromatography

Before introducing the sample comprising a mixture of organic compounds, the first column 1 is subjected to rinsing with solvent. Preferably, the solvent used is identical to that which is used for the elution step. Advantageously isooctane is used.

The sample of the mixture of organic compounds is introduced into the pump system 21 by the introduction means 23, then into the first column 1 by the connection means 20.

The sample which is introduced into the first column 1, via the introduction means 23, the pump system 21 and the connection means 20, can be a sample of the mixture of organic compounds, such as a sample of crude oil, i.e. a mixture which has undergone no prior treatment.

The sample is introduced into the column and the first eluent is introduced, by the introduction means 22, into the pump system 21 then, via the connection means 20, into the first column 1. With the elution, the aromatic and polar compounds are adsorbed by the second stationary phase 12 of the column 1 whereas the acyclic apolar compounds and, in particular the n-alkanes, are adsorbed by the first stationary phase 11.

The elution by the first eluent is carried out in isocratic mode. The first eluent or mobile phase, the composition of which is not modified during the separation step by chromatography, is iso-octane (at 100%).

The first separation step by liquid chromatography is carried out in an open column at low pressure. For this purpose, the device according to the invention advantageously comprises the means 21 allowing the first column 1 to be pressurized.

Preferably, this separation step is a separation step using so-called "flash" or low pressure chromatography. Typically, a pressure of an inert gas is applied, using the pump system 21, for circulation of the eluent along the first column 1. This applied pressure, monitored using a manometer (not shown) incorporated into the pump system 21, can in particular be comprised between 7 and 9 bars. Thus, the separation step is carried out at mobile phase flow rates that are higher than with a separation at atmospheric pressure.

The eluted fractions collected at the base of the first column 1 are then conveyed, by the connection means 24, into the detection and analysis means 25 then into collection means 26.

The eluted fractions can also be collected directly on leaving the first column 1 and subsequently analyzed. In particular, the configuration of the different elements of the device and the means used for the analysis depend on the objective sought, namely whether the separation method is to be utilized on an analytical scale or on a preparative scale.

These detection and analysis means 25 can in particular be constituted by a differential refractometer (DR), a UV detector (if it is desired to verify the absence of aromatics in the collected fractions), a flame ionization detector (FID) or also a mass spectrometer (MS).

Once the separation method is completed, the first column 1 can be detached from the device and replaced by a new column for a subsequent separation.

Optional Preparation Step

The eluted fractions such as those collected leaving the first column 1 can be subjected to a prior preparation step before the implementation of the second separation step by liquid chromatography.

This preparation step can in particular consist of a filtration and/or a concentration step, for example by partial evaporation.

Second Separation Step by Liquid Chromatography

The eluted fractions collected in the collection means 26, whether or not they have been subjected to the preparation step mentioned above, are then introduced, by the introduction means 27, into the degasser 28 then into the high pressure pump 29 and finally into the second column 2.

The second eluent, preferably a pentane/isopropanol mixture, 98/2 vol/vol, is introduced by the introduction means 30 into the degasser 28, then into the pump system 29 and finally into the second column 2 through the connection 34. This elution allows the complexing, in the stationary β-cyclodextrin phase, of the diamondoids present in the eluted fractions and their elution which is late compared with the other components of the mixture of iso-alkanes and cycloalkanes.

The elution by the second eluent is carried out in isocratic mode.

This second separation step by liquid chromatography is preferably implemented under pressure, either by means of a high performance liquid chromatography (HPLC) device, this use of HPLC being the particularly preferred route for the implementation of this second separation step. For this purpose, the device according to the invention advantageously comprises means allowing the second column 2 to be pressurized by means of the pump system 29. Typically, a pressure is applied which can in particular be comprised between 19 and 20 bars.

The eluted fractions collected at the base of the second column 2 are then conveyed, by the connection means 31, into the detection and analysis means 32 then into the collection means 33.

As during the first separation step, the eluted fractions can also be collected directly on leaving the second column 2 and subsequently analyzed. In particular, the configuration of the different elements of the device and the means used for the analysis depend on the objective sought, namely whether the separation method is to be utilized on an analytical scale or on a preparative scale.

These detection and analysis means 32 are an evaporative light scattering detector (ELSD), or a differential refractometer (DR) but the other means mentioned above, such as a UV detector, a flame ionization detector (FID) or also a mass spectrometer can also be used.

The device comprises means for automating the method, a computer 35 and software, in particular data-processing software, this computer being linked by connections 36 (partially shown) to the other elements of the device. These means allow monitoring of the introduction of the samples into the columns, and/or the recovery of the eluted fractions leaving the column, and/or monitoring of the analysis means, and/or the retrieval and storage of the analytical data.

Of course, when the initial sample is not constituted by a mixture of organic compounds, but is formed by a mixture of iso-alkanes and cycloalkanes, the separation method according to the invention is implemented only starting from the second separation step, this second step being optionally preceded by the preparation step.

EXAMPLE

Step 1

First material: mixture of organic compounds of different origins, originating from deposits of crude petroleum, shale oils, petroleum cuts.

First column: column 7.5 cm in length and 1.7 cm in diameter comprising the following three stationary phases in the quantities indicated:

the zeolite ZSM-5 as first stationary phase 11, $MP_1$=3.9-4.0 g, a silica impregnated with silver nitrate (CAS 7761-88-8) as second stationary phase 12, $MP_2$=2.3-2.4 g, and a silica grafted with cyanopropyl groups (supplied by Merck) as third stationary phase 13, $MP_3$=1.3-1.4 g.

Quantity of sample introduced into the first column: 300 μL

Generally, the injected quantity depends on the characteristics of the oil sample (in terms of percentage of n-alkanes in particular). In practice, the following rules can be adopted:

1) In the case of an oil in which the % by mass of $C_{30+}$ n-alkane is ≥1.5% (and $C_{35+}$>0.5%): max. quantity to be injected in flash chromatography: <100 mg total oil equivalent.

2) In the case of an oil in which the % by mass of n-alkane $C_{30+}$ is ≥0.5% (and $C_{35+}$>0.1%): max. quantity to be injected in flash chromatography: ~150-160 mg TO. eq.

These oils are generally diluted upstream in iso-octane (dilution factor approximately 13, for example).

3) Otherwise, injection of 250-260 mg TO. eq. (i.e. a volume of approximately 300 μL of crude oil, not diluted).

The separation method of the first step was carried out using so-called "flash" chromatography, under the particular operating conditions indicated in Table 2 below.

| | |
|---|---|
| Mobile phase | Iso-octane (100%) |
| Elution mode | isocratic |
| Flow rate | 1 or 2 ml/min |
| Temperature | ambient temperature (22° C.) |
| Pressure | 7 to 9 bars |
| Quantity injected | Between 100 and 250 mg total oil equivalent |
| Duration of the analysis | 10 min |

Step 2

β-cyclodextrin, commercial HPLC column Cyclobond I 2000—5 μm—dimensions: 250 mm×4.6 mm; supplier: Interchim (reference: 20024AST)

Quantity of sample introduced into the second column: 10 μL of the fraction of iso-alkanes and cycloalkanes recovered on leaving the first column is introduced HPLC Device 1260 (trademark Agilent).

The method for separating the second step was carried out by high performance liquid chromatography (HPLC), under the particular operating conditions indicated in Table 3 below using the device described above.

TABLE 3

| | |
|---|---|
| Mobile phase | Pentane/isopropanol (98%/2%) |
| Elution mode | isocratic |
| Flow rate | 1 ml/min |
| Temperature | ambient temperature (22° C.) |
| Pressure | 19-20 bars |
| Volume of sample injected | 10 μL-30 μL |
| Duration of the analysis | 10 min |

It can be envisaged to repeat the injection of the fraction of iso-alkanes and cycloalkanes. The successively collected fractions can then be combined, then concentrated by partial evaporation.

Figure 3:
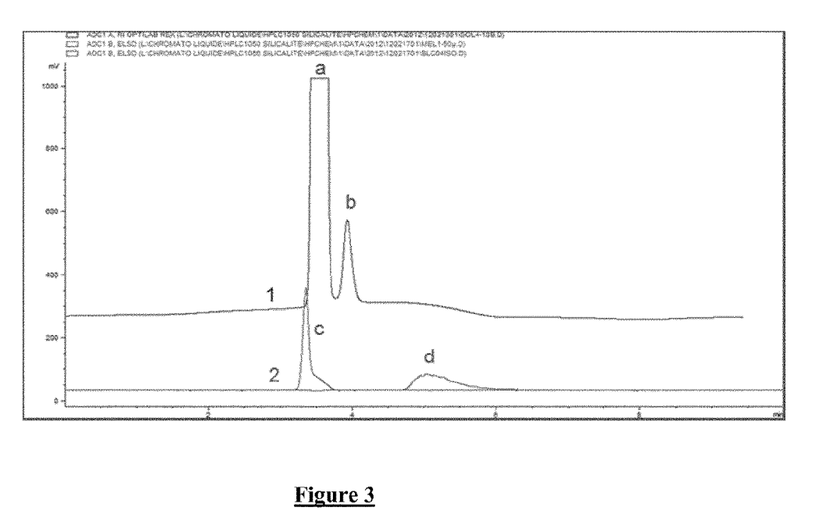

The fractions obtained are analyzed. The results are shown in FIG. 3:

The curve 1 represents the differential refractometry analysis of a solution of adamantane in iso-octane.

The curve 2 represents the ELSD (evaporative light scattering detection) analysis of a mixture of 8 standards in iso-octane (adamantane; diamantane; ααα 20R Cholestane; βαα 20R Cholestane; 17β(H), 21β(H) Hopane; Phytane (2,6,10,14-tetramethylhexadecane); Pristane (2,6,10,14-tetramethylpentadecane); 3 methyl pentadecane).

The following peaks are identified:
a: iso-octane peak.
b: adamantane peak
c: iso-octane peak and peaks of the 6 standards of isocyclo-alkanes (except adamantane and diamantane).
d: diamantane peak.

Figure 4:
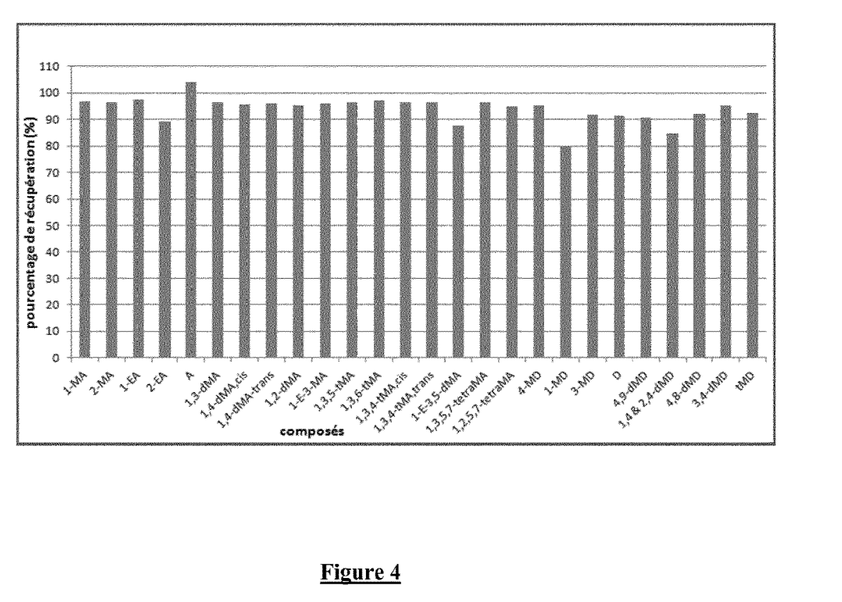
FIG. 4 is a histogram representing the total collection percentage of the diamondoids in the collected fractions leaving the column of β-cyclodextrin after implementation of the method according to the invention.

The histogram shown in FIG. 4 also shows that the fraction of the diamondoids collected comprises diamondoids in proportions which are roughly constant and greater than 80%, or even greater than 90% for the majority of these compounds, some even being close to 100%. Where columns exceed 100%, this is due to the analytical uncertainties.

It is observed that the separation method according to the invention, besides being simple to implement, selective in terms of collection of diamondoids from a fraction of iso-cycloalkanes and allowing this collection with a good yield level, is moreover rapid. By way of illustration, mention may be made of the fact that the above separation method lasted 10 minutes whereas the method of the prior art required more than 8 hours.

The invention claimed is:

1. Method for isolating diamondoids from a mixture of organic compounds by a method comprising the following steps:
   a first separation step by liquid chromatography of a fraction of iso-alkanes and cycloalkanes from the mixture of organic compounds, said mixture of organic compounds comprising iso-alkanes, cycloalkanes, n-alkanes, aromatic compounds, polar compounds, high molecular weight and/or heteroatomic compounds, and said first separation step comprising:
      introducing the mixture of organic compounds into a first single column comprising three stationary phases, the first stationary phase being of a material capable of adsorbing n-alkanes, the second stationary phase being of a material capable of adsorbing the aromatic compounds and the polar compounds, and the third stationary phase being of a material capable of adsorbing high molecular weight and/or heteroatomic compounds in which the third stationary phase comprises a silica selected from a silica grafted with aminoalkyl groups and a silica grafted with cyanoalkyl groups,
      eluting with an eluent selected from isooctane, n-octane and mixtures thereof, and
      collecting the fraction or fractions of eluted iso-alkanes and cycloalkanes, and
      in said first separation step, the third stationary phase is arranged before the second stationary phase, the second stationary phase is arranged before the first stationary phase, following the direction of elution, and
   a second separation step by liquid chromatography of the diamondoids from the said fraction or fractions of iso-alkanes and cycloalkanes, the second separation step comprising:
      introducing the sample into a second column comprising a stationary phase comprising a material capable of forming inclusion complexes with the diamondoids, said material being selected from the cyclodextrins,
      eluting with an eluent selected from mixtures of n-alkane and alkanol, and
      collecting the eluted fractions comprising the diamondoids.

2. Method according to claim 1, in which the first separation step is a separation step by low pressure chromatography, in which the liquid phase is eluted under a pressure of less than 25 bars.

3. Method according to claim 1, which comprises an intermediate step of preparation of the fraction of isoalkanes and cycloalkanes, this preparation comprising a filtration and/or a concentration by partial evaporation of the solvent.

4. Method according to claim 1 in which the mixture of organic compounds originates, directly or after treatment, from a deposit of crude oil, shale oils, or petroleum cuts.

5. Method according to claim 1, in which the first stationary phase comprises a zeolite and the second stationary phase comprises a silica impregnated with silver nitrate.

6. Method according to claim 1, in which the material capable of forming inclusion complexes with the diamondoids is β-cyclodextrin.

7. Method according to claim 1, in which the eluent is selected from mixtures of C3-C8 n-alkane and C1-C4 alkanol with an alkane/alkanol volume ratio ranging from 90/10 to 99.5/0.5.

8. Method according to claim 7, in which the eluent is a pentane/isopropanol mixture.

9. Method according to claim 8, in which the volume ratio in the pentane/isopropanol mixture is of 98%/2% vol/vol.

10. Method according to claim 1, in which the second column involved in the second separation step is an High Performance Liquid Chromatography (HPLC) column connected to an High Performance Liquid Chromatography (HPLC) device, the method being implemented with a pressure in the column ranging from 10 to 30 bars.

* * * * *